United States Patent
Corbitt, Jr.

(10) Patent No.: US 8,157,862 B2
(45) Date of Patent: *Apr. 17, 2012

(54) TISSUE MARKING IMPLANT

(75) Inventor: John D. Corbitt, Jr., Atlantis, FL (US)

(73) Assignee: Senorx, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/965,405

(22) Filed: Dec. 10, 2010

(65) Prior Publication Data

US 2011/0082547 A1 Apr. 7, 2011

Related U.S. Application Data

(60) Continuation of application No. 12/589,413, filed on Oct. 23, 2009, now Pat. No. 7,871,438, which is a division of application No. 11/108,785, filed on Apr. 19, 2005, now Pat. No. 7,637,948, which is a continuation-in-part of application No. 10/627,718, filed on Jul. 28, 2003, now Pat. No. 6,881,226, which is a continuation of application No. 09/828,806, filed on Apr. 10, 2001, now Pat. No. 6,638,308, which is a division of application No. 09/169,351, filed on Oct. 9, 1998, now Pat. No. 6,214,045.

(60) Provisional application No. 60/061,588, filed on Oct. 10, 1997, provisional application No. 60/077,639, filed on Mar. 11, 1998, provisional application No. 60/091,306, filed on Jun. 30, 1998.

(51) Int. Cl.
*A61F 2/12* (2006.01)

(52) U.S. Cl. .......................................................... 623/7
(58) Field of Classification Search .................. 623/7–8; 424/400
See application file for complete search history.

(56) References Cited

U.S. PATENT DOCUMENTS

| | | |
|---|---|---|
| 2,192,270 A | 3/1940 | McGowan |
| 2,481,408 A | 9/1949 | Fuller et al. |
| 2,832,888 A | 4/1958 | Houston |
| 2,899,362 A | 8/1959 | Sieger, Jr. et al. |
| 2,907,327 A | 10/1959 | White |
| 3,341,417 A | 9/1967 | Sinaiko |
| 3,402,712 A | 9/1968 | Eisenhand |
| 3,516,412 A | 6/1970 | Ackerman |
| 3,593,343 A | 7/1971 | Viggers |
| 3,757,781 A | 9/1973 | Smart |
| 3,818,894 A | 6/1974 | Wichterle et al. |

(Continued)

FOREIGN PATENT DOCUMENTS

DE 1029528 B 5/1958

(Continued)

OTHER PUBLICATIONS

Eiselt, P. et al, "Development of Technologies Aiding Large-Tissue Engineering", Biotechnol. Prog., vol. 14, No. 1, pp. 134-140, 1998.

(Continued)

*Primary Examiner* — Suzette J Gherbi

(57) ABSTRACT

An implant for marking an area within a living body includes a matrix material and a marking material. The implant is formable to fit the shape and size of a cavity in the human body. The implant is configured to support tissue surrounding the cavity and to allow in-growth of fibrous tissue into and replace at least a portion of the matrix material.

7 Claims, 1 Drawing Sheet

U.S. PATENT DOCUMENTS

| | | |
|---|---|---|
| 3,823,212 A | 7/1974 | Chvapil |
| 3,921,632 A | 11/1975 | Bardani |
| 4,005,699 A | 2/1977 | Bucalo |
| 4,007,732 A | 2/1977 | Kvavle et al. |
| 4,041,931 A | 8/1977 | Elliott et al. |
| 4,103,690 A | 8/1978 | Harris |
| 4,105,030 A | 8/1978 | Kercso |
| 4,172,449 A | 10/1979 | LeRoy et al. |
| 4,197,846 A | 4/1980 | Bucalo |
| 4,217,889 A | 8/1980 | Radovan et al. |
| 4,276,885 A | 7/1981 | Tickner et al. |
| 4,294,241 A | 10/1981 | Miyata |
| 4,298,998 A | 11/1981 | Naficy |
| 4,331,654 A | 5/1982 | Morris |
| 4,390,018 A | 6/1983 | Zukowski |
| 4,400,170 A | 8/1983 | McNaughton et al. |
| 4,401,124 A | 8/1983 | Guess et al. |
| 4,405,314 A | 9/1983 | Cope |
| 4,428,082 A | 1/1984 | Naficy |
| 4,438,253 A | 3/1984 | Casey et al. |
| 4,442,843 A | 4/1984 | Rasor et al. |
| 4,470,160 A | 9/1984 | Cavon |
| 4,487,209 A | 12/1984 | Mehl |
| 4,545,367 A | 10/1985 | Tucci |
| 4,549,560 A | 10/1985 | Andis |
| 4,582,061 A | 4/1986 | Fry |
| 4,582,640 A * | 4/1986 | Smestad et al. ............... 530/356 |
| 4,588,395 A | 5/1986 | Lemelson |
| 4,597,753 A | 7/1986 | Turley |
| 4,647,480 A | 3/1987 | Ahmed |
| 4,655,226 A | 4/1987 | Lee |
| 4,661,103 A | 4/1987 | Harman |
| 4,682,606 A | 7/1987 | DeCaprio |
| 4,693,237 A | 9/1987 | Hoffman et al. |
| 4,740,208 A | 4/1988 | Cavon |
| 4,813,062 A | 3/1989 | Gilpatrick |
| 4,820,267 A | 4/1989 | Harman |
| 4,832,680 A | 5/1989 | Haber et al. |
| 4,832,686 A | 5/1989 | Anderson |
| 4,847,049 A | 7/1989 | Yamamoto |
| 4,863,470 A | 9/1989 | Carter |
| 4,870,966 A | 10/1989 | Dellon et al. |
| 4,874,376 A | 10/1989 | Hawkins, Jr. |
| 4,889,707 A | 12/1989 | Day et al. |
| 4,909,250 A | 3/1990 | Smith |
| 4,938,763 A * | 7/1990 | Dunn et al. ............... 604/891.1 |
| 4,950,665 A | 8/1990 | Floyd |
| 4,963,150 A | 10/1990 | Brauman |
| 4,970,298 A * | 11/1990 | Silver et al. ............... 530/356 |
| 4,989,608 A | 2/1991 | Ratner |
| 4,994,028 A | 2/1991 | Leonard et al. |
| 5,012,818 A | 5/1991 | Joishy |
| 5,059,197 A | 10/1991 | Urie et al. |
| 5,081,997 A | 1/1992 | Bosley, Jr. et al. |
| 5,120,802 A | 6/1992 | Mares et al. |
| 5,125,413 A | 6/1992 | Baran |
| 5,137,928 A | 8/1992 | Erbel et al. |
| 5,141,748 A | 8/1992 | Rizzo |
| 5,147,307 A | 9/1992 | Gluck |
| 5,147,631 A | 9/1992 | Glajch et al. |
| 5,162,430 A | 11/1992 | Rhee et al. |
| 5,163,896 A | 11/1992 | Suthanthiran et al. |
| 5,195,540 A | 3/1993 | Shiber |
| 5,197,846 A | 3/1993 | Uno et al. |
| 5,199,441 A | 4/1993 | Hogle |
| 5,219,339 A | 6/1993 | Saito |
| 5,221,269 A | 6/1993 | Miller et al. |
| 5,231,615 A | 7/1993 | Endoh |
| 5,236,410 A | 8/1993 | Granov et al. |
| 5,242,759 A | 9/1993 | Hall |
| 5,250,026 A | 10/1993 | Ehrlich et al. |
| 5,271,961 A | 12/1993 | Mathiowitz et al. |
| 5,273,532 A | 12/1993 | Niezink et al. |
| 5,280,788 A | 1/1994 | Janes et al. |
| 5,281,197 A | 1/1994 | Arias et al. |
| 5,281,408 A | 1/1994 | Unger |
| 5,282,781 A | 2/1994 | Liprie |
| 5,284,479 A | 2/1994 | de Jong |
| 5,289,831 A | 3/1994 | Bosley |
| 5,320,613 A | 6/1994 | Houge et al. |
| 5,328,955 A | 7/1994 | Rhee et al. |
| 5,334,381 A | 8/1994 | Unger |
| 5,353,804 A | 10/1994 | Kornberg et al. |
| 5,354,623 A | 10/1994 | Hall |
| 5,366,756 A * | 11/1994 | Chesterfield et al. ........ 427/2.26 |
| 5,368,030 A | 11/1994 | Zinreich et al. |
| 5,388,588 A | 2/1995 | Nabai et al. |
| 5,394,875 A | 3/1995 | Lewis et al. |
| 5,395,319 A | 3/1995 | Hirsch et al. |
| 5,409,004 A | 4/1995 | Sloan |
| 5,417,708 A | 5/1995 | Hall et al. |
| 5,422,730 A | 6/1995 | Barlow et al. |
| 5,425,366 A | 6/1995 | Reinhardt et al. |
| 5,433,204 A | 7/1995 | Olson |
| 5,449,560 A | 9/1995 | Antheunis et al. |
| 5,451,406 A | 9/1995 | Lawin et al. |
| 5,460,182 A | 10/1995 | Goodman et al. |
| 5,469,847 A | 11/1995 | Zinreich et al. |
| 5,475,052 A | 12/1995 | Rhee et al. |
| 5,490,521 A | 2/1996 | Davis et al. |
| 5,494,030 A | 2/1996 | Swartz et al. |
| 5,499,989 A | 3/1996 | LaBash |
| 5,507,807 A | 4/1996 | Shippert |
| 5,508,021 A | 4/1996 | Grinstaff et al. |
| 5,514,085 A | 5/1996 | Yoon |
| 5,522,896 A | 6/1996 | Prescott |
| 5,538,726 A | 7/1996 | Order |
| 5,542,915 A | 8/1996 | Edwards et al. |
| 5,549,560 A | 8/1996 | Van de Wijdeven |
| RE35,391 E | 12/1996 | Brauman |
| 5,580,568 A | 12/1996 | Greff et al. |
| 5,585,112 A | 12/1996 | Unger et al. |
| 5,611,352 A | 3/1997 | Kobren et al. |
| 5,626,611 A | 5/1997 | Liu et al. |
| 5,628,781 A | 5/1997 | Williams et al. |
| 5,629,008 A | 5/1997 | Lee |
| 5,636,255 A | 6/1997 | Ellis |
| 5,643,246 A | 7/1997 | Leeb et al. |
| 5,646,146 A | 7/1997 | Faarup et al. |
| 5,667,767 A | 9/1997 | Greff et al. |
| 5,673,841 A | 10/1997 | Schulze et al. |
| 5,676,146 A * | 10/1997 | Scarborough ............... 600/431 |
| 5,676,925 A | 10/1997 | Klaveness et al. |
| 5,688,490 A | 11/1997 | Tournier et al. |
| 5,690,120 A | 11/1997 | Jacobsen et al. |
| 5,695,480 A | 12/1997 | Evans et al. |
| 5,702,128 A | 12/1997 | Maxim et al. |
| 5,702,716 A | 12/1997 | Dunn et al. |
| 5,747,060 A | 5/1998 | Sackler et al. |
| 5,762,903 A | 6/1998 | Park et al. |
| 5,769,086 A | 6/1998 | Ritchart et al. |
| 5,776,496 A | 7/1998 | Violante et al. |
| 5,779,647 A | 7/1998 | Chau et al. |
| 5,782,764 A | 7/1998 | Werne |
| 5,782,775 A | 7/1998 | Milliman et al. |
| 5,795,308 A | 8/1998 | Russin |
| 5,800,362 A | 9/1998 | Kobren et al. |
| 5,800,389 A | 9/1998 | Burney et al. |
| 5,800,445 A | 9/1998 | Ratcliff et al. |
| 5,800,541 A | 9/1998 | Rhee et al. |
| 5,817,022 A | 10/1998 | Vesely |
| 5,820,918 A | 10/1998 | Ronan et al. |
| 5,821,184 A | 10/1998 | Haines et al. |
| 5,823,198 A | 10/1998 | Jones et al. |
| 5,824,042 A * | 10/1998 | Lombardi et al. ............ 623/1.13 |
| 5,824,081 A | 10/1998 | Knapp et al. |
| 5,830,178 A | 11/1998 | Jones et al. |
| 5,842,477 A | 12/1998 | Naughton et al. |
| 5,842,999 A | 12/1998 | Pruitt et al. |
| 5,845,646 A | 12/1998 | Lemelson |
| 5,846,220 A | 12/1998 | Elsberry |
| 5,851,508 A | 12/1998 | Greff et al. |
| 5,853,366 A | 12/1998 | Dowlatshahi |
| 5,865,806 A | 2/1999 | Howell |
| 5,869,080 A | 2/1999 | McGregor et al. |
| 5,876,340 A | 3/1999 | Tu et al. |
| 5,879,357 A | 3/1999 | Heaton et al. |

| Patent No. | Date | Inventor |
|---|---|---|
| 5,891,558 A * | 4/1999 | Bell et al. ................ 428/218 |
| 5,897,507 A | 4/1999 | Kortenbach et al. |
| 5,902,310 A | 5/1999 | Foerster et al. |
| 5,911,705 A | 6/1999 | Howell |
| 5,921,933 A | 7/1999 | Sarkis et al. |
| 5,922,024 A | 7/1999 | Janzen et al. |
| 5,928,626 A | 7/1999 | Klaveness et al. |
| 5,928,773 A | 7/1999 | Andersen |
| 5,941,890 A | 8/1999 | Voegele et al. |
| 5,942,209 A | 8/1999 | Leavitt et al. |
| 5,948,425 A | 9/1999 | Janzen et al. |
| 5,954,670 A | 9/1999 | Baker |
| 5,972,817 A | 10/1999 | Haines et al. |
| 5,989,265 A | 11/1999 | Bouquet De La Joliniere et al. |
| 6,015,541 A | 1/2000 | Greff et al. |
| 6,030,333 A | 2/2000 | Sioshansi et al. |
| 6,053,925 A | 4/2000 | Barnhart |
| 6,056,700 A | 5/2000 | Burney et al. |
| 6,066,122 A | 5/2000 | Fisher |
| 6,066,325 A | 5/2000 | Wallace et al. |
| 6,071,301 A | 6/2000 | Cragg et al. |
| 6,071,310 A | 6/2000 | Picha et al. |
| 6,071,496 A | 6/2000 | Stein et al. |
| 6,096,065 A | 8/2000 | Crowley |
| 6,096,070 A | 8/2000 | Ragheb et al. |
| 6,106,473 A | 8/2000 | Violante et al. |
| 6,117,108 A | 9/2000 | Woehr et al. |
| 6,120,536 A | 9/2000 | Ding et al. |
| 6,142,955 A | 11/2000 | Farascioni et al. |
| 6,159,445 A | 12/2000 | Klaveness et al. |
| 6,161,034 A | 12/2000 | Burbank et al. |
| 6,162,192 A | 12/2000 | Cragg et al. |
| 6,174,330 B1 | 1/2001 | Stinson |
| 6,177,062 B1 | 1/2001 | Stein et al. |
| 6,181,960 B1 | 1/2001 | Jensen et al. |
| 6,183,497 B1 | 2/2001 | Sing et al. |
| 6,190,350 B1 | 2/2001 | Davis et al. |
| 6,200,258 B1 | 3/2001 | Slater et al. |
| 6,203,524 B1 | 3/2001 | Burney et al. |
| 6,203,568 B1 | 3/2001 | Lombardi et al. |
| 6,213,957 B1 | 4/2001 | Milliman et al. |
| 6,214,045 B1 * | 4/2001 | Corbitt et al. ................ 623/8 |
| 6,214,315 B1 | 4/2001 | Greff et al. |
| 6,220,248 B1 | 4/2001 | Voegele et al. |
| 6,224,630 B1 | 5/2001 | Bao et al. |
| 6,228,049 B1 | 5/2001 | Schroeder et al. |
| 6,228,055 B1 | 5/2001 | Foerster et al. |
| 6,231,615 B1 | 5/2001 | Preissman |
| 6,234,177 B1 | 5/2001 | Barsch |
| 6,241,687 B1 | 6/2001 | Voegele et al. |
| 6,241,734 B1 | 6/2001 | Scribner et al. |
| 6,251,418 B1 | 6/2001 | Ahern et al. |
| 6,261,243 B1 | 7/2001 | Burney et al. |
| 6,261,302 B1 | 7/2001 | Voegele et al. |
| 6,264,917 B1 | 7/2001 | Klaveness et al. |
| 6,270,464 B1 | 8/2001 | Fulton, III et al. |
| 6,270,472 B1 | 8/2001 | Antaki et al. |
| 6,287,278 B1 | 9/2001 | Woehr et al. |
| 6,287,332 B1 | 9/2001 | Bolz et al. |
| 6,289,229 B1 | 9/2001 | Crowley |
| 6,312,429 B1 | 11/2001 | Burbank et al. |
| 6,316,522 B1 | 11/2001 | Loomis et al. |
| 6,335,029 B1 | 1/2002 | Kamath et al. |
| 6,336,904 B1 | 1/2002 | Nikolchev |
| 6,340,367 B1 | 1/2002 | Stinson et al. |
| 6,343,227 B1 | 1/2002 | Crowley |
| 6,347,240 B1 | 2/2002 | Foley et al. |
| 6,347,241 B2 | 2/2002 | Burbank et al. |
| 6,350,244 B1 | 2/2002 | Fisher |
| 6,350,274 B1 | 2/2002 | Li |
| 6,354,989 B1 | 3/2002 | Nudeshima |
| 6,356,112 B1 | 3/2002 | Tran et al. |
| 6,356,782 B1 | 3/2002 | Sirimanne et al. |
| 6,358,217 B1 | 3/2002 | Bourassa |
| 6,363,940 B1 | 4/2002 | Krag |
| 6,371,904 B1 | 4/2002 | Sirimanne et al. |
| 6,394,965 B1 | 5/2002 | Klein |
| 6,403,758 B1 | 6/2002 | Loomis |
| 6,405,733 B1 | 6/2002 | Fogarty et al. |
| 6,409,742 B1 | 6/2002 | Fulton, III et al. |
| 6,424,857 B1 | 7/2002 | Henrichs et al. |
| 6,425,903 B1 | 7/2002 | Voegele |
| 6,450,937 B1 | 9/2002 | Mercereau et al. |
| 6,450,938 B1 | 9/2002 | Miller |
| 6,471,700 B1 | 10/2002 | Burbank et al. |
| 6,478,790 B2 | 11/2002 | Bardani |
| 6,506,156 B1 | 1/2003 | Jones et al. |
| 6,511,468 B1 | 1/2003 | Cragg et al. |
| 6,537,193 B1 | 3/2003 | Lennox |
| 6,540,981 B2 | 4/2003 | Klaveness et al. |
| 6,544,185 B2 | 4/2003 | Montegrande |
| 6,551,253 B2 | 4/2003 | Worm et al. |
| 6,554,760 B2 | 4/2003 | Lamoureux et al. |
| 6,562,317 B2 | 5/2003 | Greff et al. |
| 6,564,806 B1 | 5/2003 | Fogarty et al. |
| 6,565,551 B1 | 5/2003 | Jones et al. |
| 6,575,888 B2 | 6/2003 | Zamora et al. |
| 6,575,991 B1 | 6/2003 | Chesbrough et al. |
| 6,605,047 B2 | 8/2003 | Zarins et al. |
| 6,610,026 B2 | 8/2003 | Cragg et al. |
| 6,613,002 B1 | 9/2003 | Clark et al. |
| 6,616,630 B1 | 9/2003 | Woehr et al. |
| 6,626,850 B1 | 9/2003 | Chau et al. |
| 6,628,982 B1 | 9/2003 | Thomas et al. |
| 6,636,758 B2 | 10/2003 | Sanchez et al. |
| 6,638,234 B2 | 10/2003 | Burbank et al. |
| 6,638,308 B2 | 10/2003 | Corbitt, Jr. et al. |
| 6,652,442 B2 | 11/2003 | Gatto |
| 6,656,192 B2 | 12/2003 | Espositio et al. |
| 6,699,205 B2 | 3/2004 | Fulton, III et al. |
| 6,712,774 B2 | 3/2004 | Voegele et al. |
| 6,712,836 B1 | 3/2004 | Berg et al. |
| 6,716,444 B1 | 4/2004 | Castro et al. |
| 6,725,083 B1 | 4/2004 | Burbank et al. |
| 6,730,042 B2 | 5/2004 | Fulton et al. |
| 6,730,044 B2 | 5/2004 | Stephens et al. |
| 6,746,661 B2 | 6/2004 | Kaplan |
| 6,746,773 B2 | 6/2004 | Llanos et al. |
| 6,752,154 B2 | 6/2004 | Fogarty et al. |
| 6,766,186 B1 | 7/2004 | Hoyns et al. |
| 6,774,278 B1 | 8/2004 | Ragheb et al. |
| 6,780,179 B2 | 8/2004 | Lee et al. |
| 6,824,507 B2 | 11/2004 | Miller |
| 6,824,527 B2 | 11/2004 | Gollobin |
| 6,846,320 B2 | 1/2005 | Ashby et al. |
| 6,862,470 B2 | 3/2005 | Burbank et al. |
| 6,863,685 B2 | 3/2005 | Davila et al. |
| 6,899,731 B2 | 5/2005 | Li et al. |
| 6,918,927 B2 | 7/2005 | Bates et al. |
| 6,936,014 B2 | 8/2005 | Vetter et al. |
| 6,939,318 B2 | 9/2005 | Stenzel |
| 6,945,973 B2 | 9/2005 | Bray |
| 6,951,564 B2 | 10/2005 | Espositio et al. |
| 6,994,712 B1 | 2/2006 | Fisher et al. |
| 7,001,341 B2 | 2/2006 | Gellman et al. |
| 7,008,382 B2 | 3/2006 | Adams et al. |
| 7,014,610 B2 | 3/2006 | Koulik |
| 7,025,765 B2 | 4/2006 | Balbierz et al. |
| 7,044,957 B2 | 5/2006 | Foerster et al. |
| 7,083,576 B2 | 8/2006 | Zarins et al. |
| 7,125,397 B2 | 10/2006 | Woehr et al. |
| 7,172,549 B2 | 2/2007 | Slater et al. |
| 7,214,211 B2 | 5/2007 | Woehr et al. |
| 7,229,417 B2 | 6/2007 | Foerster et al. |
| 7,236,816 B2 | 6/2007 | Kumar et al. |
| 7,264,613 B2 | 9/2007 | Woehr et al. |
| 7,294,118 B2 | 11/2007 | Saulenas et al. |
| 7,297,725 B2 | 11/2007 | Winterton et al. |
| 7,329,402 B2 | 2/2008 | Unger et al. |
| 7,416,533 B2 | 8/2008 | Gellman et al. |
| 7,424,320 B2 | 9/2008 | Chesbrough et al. |
| 7,449,000 B2 | 11/2008 | Adams et al. |
| 7,527,610 B2 | 5/2009 | Erickson |
| 7,534,452 B2 | 5/2009 | Chernomorsky et al. |
| 7,569,065 B2 | 8/2009 | Chesbrough et al. |
| 7,819,820 B2 | 10/2010 | Field et al. |
| 2001/0006616 A1 | 7/2001 | Leavitt et al. |
| 2002/0004060 A1 | 1/2002 | Heublein et al. |

| | | |
|---|---|---|
| 2002/0016625 A1 | 2/2002 | Falotico et al. |
| 2002/0022883 A1 | 2/2002 | Burg |
| 2002/0026201 A1 | 2/2002 | Foerster et al. |
| 2002/0035324 A1 | 3/2002 | Sirimanne et al. |
| 2002/0045842 A1 | 4/2002 | Van Bladel et al. |
| 2002/0052572 A1 | 5/2002 | Franco et al. |
| 2002/0055731 A1 | 5/2002 | Atala et al. |
| 2002/0058868 A1 | 5/2002 | Hoshino et al. |
| 2002/0058882 A1 | 5/2002 | Fulton, III et al. |
| 2002/0077687 A1 | 6/2002 | Ahn |
| 2002/0082519 A1 | 6/2002 | Miller et al. |
| 2002/0082682 A1 | 6/2002 | Barclay et al. |
| 2002/0082683 A1 | 6/2002 | Stinson et al. |
| 2002/0095204 A1 | 7/2002 | Thompson et al. |
| 2002/0095205 A1 | 7/2002 | Edwin et al. |
| 2002/0107437 A1 | 8/2002 | Sirimanne et al. |
| 2002/0133148 A1 | 9/2002 | Daniel et al. |
| 2002/0143359 A1 | 10/2002 | Fulton, III et al. |
| 2002/0165608 A1 | 11/2002 | Llanos et al. |
| 2002/0193815 A1 | 12/2002 | Foerster et al. |
| 2002/0193867 A1 | 12/2002 | Gladdish, Jr. et al. |
| 2003/0036803 A1 | 2/2003 | McGhan |
| 2003/0051735 A1 | 3/2003 | Pavcnik et al. |
| 2003/0116806 A1 | 6/2003 | Kato |
| 2003/0165478 A1 | 9/2003 | Sokoll |
| 2003/0191355 A1 | 10/2003 | Ferguson |
| 2003/0199887 A1 | 10/2003 | Ferrera et al. |
| 2003/0225420 A1 | 12/2003 | Wardle |
| 2003/0236573 A1 | 12/2003 | Evans et al. |
| 2004/0002650 A1 | 1/2004 | Mandrusov et al. |
| 2004/0016195 A1 | 1/2004 | Archuleta |
| 2004/0024304 A1 | 2/2004 | Foerster et al. |
| 2004/0059341 A1 | 3/2004 | Gellman et al. |
| 2004/0073107 A1 | 4/2004 | Sioshansi et al. |
| 2004/0073284 A1 | 4/2004 | Bates et al. |
| 2004/0097981 A1 | 5/2004 | Selis |
| 2004/0101479 A1 | 5/2004 | Burbank et al. |
| 2004/0106891 A1 | 6/2004 | Langan et al. |
| 2004/0116802 A1 | 6/2004 | Jessop et al. |
| 2004/0124105 A1 | 7/2004 | Seiler et al. |
| 2004/0127765 A1 | 7/2004 | Seiler et al. |
| 2004/0162574 A1 | 8/2004 | Viola |
| 2004/0167619 A1 | 8/2004 | Case et al. |
| 2004/0204660 A1 | 10/2004 | Fulton et al. |
| 2004/0210208 A1 | 10/2004 | Paul et al. |
| 2004/0213756 A1 | 10/2004 | Michal et al. |
| 2005/0020916 A1 | 1/2005 | MacFarlane et al. |
| 2005/0033157 A1 | 2/2005 | Klien et al. |
| 2005/0033195 A1 | 2/2005 | Fulton et al. |
| 2005/0036946 A1 | 2/2005 | Pathak et al. |
| 2005/0045192 A1 | 3/2005 | Fulton et al. |
| 2005/0059887 A1 | 3/2005 | Mostafavi et al. |
| 2005/0059888 A1 | 3/2005 | Sirimanne et al. |
| 2005/0065354 A1 | 3/2005 | Roberts |
| 2005/0065453 A1 | 3/2005 | Shabaz et al. |
| 2005/0080337 A1 | 4/2005 | Sirimanne et al. |
| 2005/0080339 A1* | 4/2005 | Sirimanne et al. ............ 600/431 |
| 2005/0085724 A1 | 4/2005 | Sirimanne et al. |
| 2005/0100580 A1 | 5/2005 | Osborne et al. |
| 2005/0113659 A1 | 5/2005 | Pothier et al. |
| 2005/0119562 A1 | 6/2005 | Jones et al. |
| 2005/0143650 A1 | 6/2005 | Winkel |
| 2005/0165305 A1 | 7/2005 | Foerster et al. |
| 2005/0175657 A1 | 8/2005 | Hunter et al. |
| 2005/0181007 A1 | 8/2005 | Hunter et al. |
| 2005/0234336 A1 | 10/2005 | Beckman et al. |
| 2005/0268922 A1 | 12/2005 | Conrad et al. |
| 2005/0273002 A1 | 12/2005 | Goosen et al. |
| 2005/0277871 A1 | 12/2005 | Selis |
| 2006/0004440 A1 | 1/2006 | Stinson |
| 2006/0009800 A1 | 1/2006 | Christianson et al. |
| 2006/0036158 A1 | 2/2006 | Field et al. |
| 2006/0036159 A1* | 2/2006 | Sirimanne et al. ............ 600/414 |
| 2006/0074443 A1 | 4/2006 | Foerster et al. |
| 2006/0079770 A1 | 4/2006 | Sirimanne et al. |
| 2006/0079805 A1 | 4/2006 | Miller et al. |
| 2006/0079829 A1 | 4/2006 | Fulton et al. |
| 2006/0079888 A1 | 4/2006 | Mulier et al. |
| 2006/0122503 A1 | 6/2006 | Burbank et al. |
| 2006/0155190 A1 | 7/2006 | Burbank et al. |
| 2006/0173280 A1 | 8/2006 | Goosen et al. |
| 2006/0173296 A1 | 8/2006 | Miller et al. |
| 2006/0177379 A1 | 8/2006 | Asgari |
| 2006/0217635 A1 | 9/2006 | McCombs et al. |
| 2006/0235298 A1 | 10/2006 | Kotmel et al. |
| 2006/0241385 A1 | 10/2006 | Dietz |
| 2007/0021642 A1 | 1/2007 | Lamoureux et al. |
| 2007/0083132 A1 | 4/2007 | Sharrow |
| 2007/0135711 A1 | 6/2007 | Chernomorsky et al. |
| 2007/0142725 A1 | 6/2007 | Hardin et al. |
| 2007/0167736 A1 | 7/2007 | Dietz et al. |
| 2007/0167749 A1 | 7/2007 | Yarnall et al. |
| 2007/0239118 A1 | 10/2007 | Ono et al. |
| 2007/0287933 A1 | 12/2007 | Phan et al. |
| 2008/0097199 A1 | 4/2008 | Mullen |
| 2008/0188768 A1 | 8/2008 | Zarins et al. |
| 2008/0269638 A1 | 10/2008 | Cooke et al. |
| 2009/0000629 A1 | 1/2009 | Hornscheidt et al. |
| 2009/0024225 A1 | 1/2009 | Stubbs |
| 2009/0069713 A1 | 3/2009 | Adams et al. |
| 2009/0076484 A1 | 3/2009 | Fukaya |
| 2009/0131825 A1 | 5/2009 | Burbank et al. |

FOREIGN PATENT DOCUMENTS

| | | |
|---|---|---|
| EP | 0146699 A1 | 7/1985 |
| EP | 0255123 A2 | 2/1988 |
| EP | 0292936 A2 | 11/1988 |
| EP | 0458745 A1 | 11/1991 |
| EP | 0552924 A1 | 7/1993 |
| EP | 0475077 B1 | 12/1996 |
| EP | 0769281 A2 | 4/1997 |
| EP | 1114618 A2 | 1/2001 |
| EP | 1163888 A1 | 12/2001 |
| EP | 1281416 A2 | 6/2002 |
| EP | 1364628 A1 | 11/2003 |
| EP | 1493451 A1 | 1/2005 |
| EP | 1767167 A2 | 3/2007 |
| FR | 2646674 A3 | 11/1990 |
| GB | 708148 | 4/1954 |
| JP | 2131757 A | 5/1990 |
| WO | 8906978 A1 | 8/1989 |
| WO | 9112823 A1 | 9/1991 |
| WO | 9314712 A1 | 8/1993 |
| WO | 9317671 A1 | 9/1993 |
| WO | 9317718 A1 | 9/1993 |
| WO | 9416647 A1 | 8/1994 |
| WO | 9507057 A1 | 9/1994 |
| WO | 9806346 A1 | 2/1998 |
| WO | 9908607 A1 | 2/1999 |
| WO | 9935966 A1 | 7/1999 |
| WO | 9951143 A1 | 10/1999 |
| WO | 0023124 A1 | 4/2000 |
| WO | 0024332 A1 | 5/2000 |
| WO | 0028554 A1 | 5/2000 |
| WO | 0054689 A1 | 9/2000 |
| WO | 0108578 A1 | 2/2001 |
| WO | 0170114 A1 | 9/2001 |
| WO | 0207786 A2 | 1/2002 |
| WO | 0241786 A2 | 5/2002 |
| WO | 03000308 A1 | 1/2003 |
| WO | 2004045444 A2 | 6/2004 |
| WO | 2005013832 A1 | 2/2005 |
| WO | 2005089664 A1 | 9/2005 |
| WO | 2006056739 A2 | 6/2006 |
| WO | 2006097331 A2 | 9/2006 |
| WO | 2006105353 A2 | 10/2006 |
| WO | 2007069105 A2 | 6/2007 |
| WO | 2008077081 A2 | 6/2008 |

OTHER PUBLICATIONS

Armstong, J.S., et al., "Differential marking of Excision Planes in Screened Breast lesions By Organically Coloured Gelatins", Journal of Clinical Pathology, Jul. 1990, No. 43 (7) pp. 604-607, XP000971447 abstract; tables 1,2.

Fucci, V., et al., "Large Bowel Transit Times Using Radioopaque Markers in Normal Cats", J. of Am. Animal Hospital Assn., Nov.-Dec. 1995 31 (6) 473-477.

Schindlbeck, N.E., et al., "Measurement of Colon Transit Time", J. of Gastroenterology, No. 28, pp. 399-404, 1990.

Shiga, et al., Preparation of Poly(D, L-lactide) and Copoly(lactide-glycolide) Microspheres of Uniform Size, J. Pharm. Pharmacol. 1996 48:891-895.

Press release for Biopsys Ethicon Endo-Surgery (Europe) GmbH; The Mammotome Vacuum Biopsy System. From: http://www.medicine-news.com/articles/devices/mammotome.html. 3 pages.

Johnson & Johnson: Breast Biopsy (minimally invasive): Surgical Technique: Steps in the MAMOTOME Surgical Procedure. From http://www.jnjgateway.com. 3 pages.

Johnson & Johnson: New Minimally Invasive Breast Biopsy Device Receives Marketing Clearance in Canada; Aug. 6, 1999. From http://www.jnjgateway.com. 4 pages.

Johnson & Johnson: Mammotome Hand Held Receives FDA Marketing Clearance for Minimally Invasive Breast Biopises; Sep. 1, 1999. From From http://www.jnjgateway.com. 5 pages.

Johnson & Johnson: The Mammotome Breast Biopsy System. From: http://www.breastcareinfo.com/aboutm.htm. 6 pages.

Cook Incorporated: Emoblization and Occlusion. From: www.cookgroup.com 6 pages.

Liberman, Laura, et al. Percutaneous Removal of Malignant Mammographic Lesions at Stereotactic Vacuum-assisted Biopsy. From: The Departments of Radiology, Pathology, and Surgery. Memorial Sloan-Kettering Cancer Center. From the 1997 RSNA scientific assembly. vol. 206, No. 3. pp. 711-715.

* cited by examiner

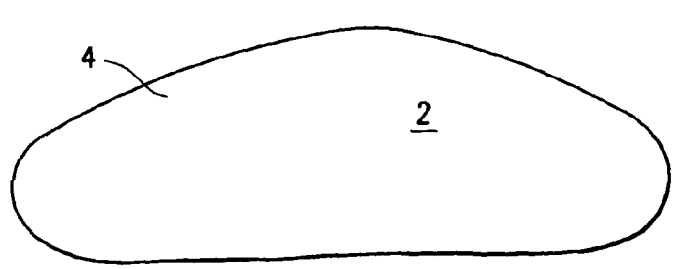
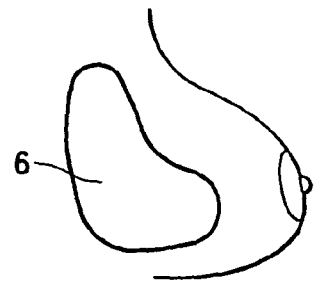
FIG. 1  FIG. 2
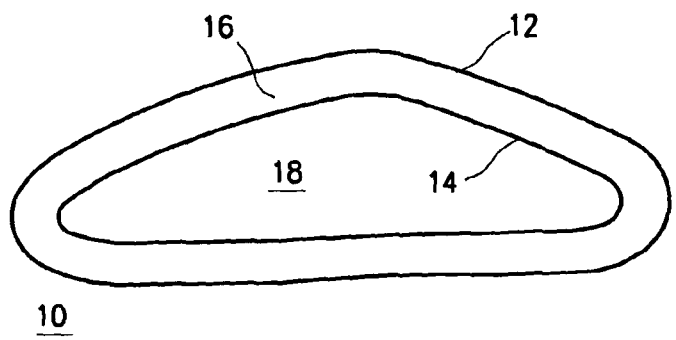
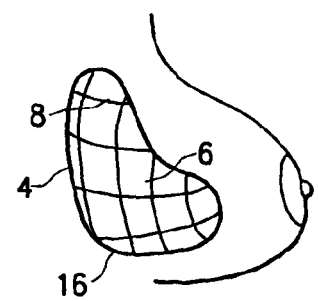
FIG. 4  FIG. 3
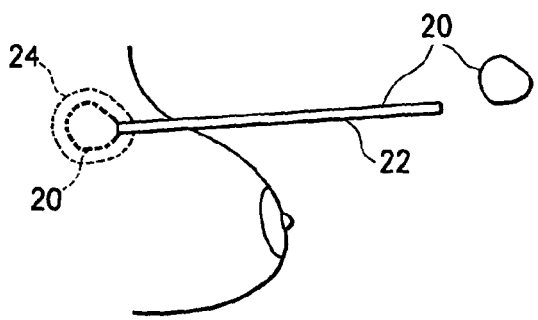
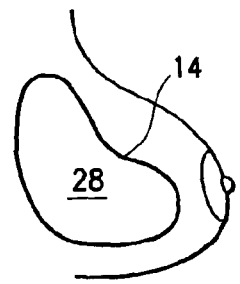
FIG. 6  FIG. 5

TISSUE MARKING IMPLANT

CROSS REFERENCE TO RELATED APPLICATIONS

This application is continuation of application Ser. No. 12/589,413, filed Oct. 23, 2009, now U.S. Pat. No. 7,871,438, which is a divisional of application Ser. No. 11/108,785, filed Apr. 19, 2005, now U.S. Pat. No. 7,637,948, which is a continuation-in-part of U.S. patent application Ser. No. 10/627,718, filed Jul. 28, 2003, now U.S. Pat. No. 6,881,226, which is continuation of application Ser. No. 09/828,806, filed Apr. 10, 2001, now U.S. Pat. No. 6,638,308, which is a divisional of U.S. patent application Ser. No. 09/169,351, filed Oct. 9, 1998, now U.S. Pat. No. 6,214,045, which claims the benefit of U.S. Provisional Application Ser. No. 60/061, 588, filed Oct. 10, 1997, U.S. Provisional Application Ser. No. 60/077,639, filed Mar. 11, 1998, and U.S. Provisional Application Ser. No. 60/091,306, filed Jun. 30, 1998, the disclosures of which are incorporated herein by reference.

BACKGROUND OF THE INVENTION

1. Field of the Invention

The present invention relates to implantable prostheses. More particularly, the present invention relates to implantable breast prostheses designed to eliminate encapsulation and reduce scarring, and to replace tissue removed for purposes of biopsy or lumpectomy.

2. Description of the Related Art

Breast prostheses are utilized for augmentation mammoplasty and in cosmetic surgery. Prostheses are also indicated in breast cancer surgery, such as lumpectomies, where a portion of the breast is removed and can leave some disfigurement if not replaced by a similar amount of tissue and/or augmentation material.

Similarly, biopsies can leave small dimples or imperfections if remedial steps are not taken. About 1 million breast biopsies are performed in the United States annually. As a result, some 200,000 new breast cancers are diagnosed each year.

Known methods of augmentation mammoplasty utilize silicone or saline implants. These methods have been complicated post-operatively by encapsulation of the implants, which can occur to varying degrees. Encapsulation produces a hard area of scar tissue around the implant, resulting in a rigid, abnormally-shaped mount beneath the breast tissue or pectoralis muscle, depending upon the placement of the implant.

Moreover, the known implant materials may not be indicated for replacement of smaller amounts of tissue, as would be required to prevent dimpling after biopsies, for example. Further, the known implant materials are not amenable to resizing. In addition, known implants are not capable of being implanted through a cannula or needle, and are not readily instilled with medicaments or chemical agents that would be useful in treating the patient.

Accordingly, a need exists for implants and methods that can be adapted for replacement of small as well as large amounts of tissue. A need also exists for implants that can be delivered through cannulae or needles, as well as being able to significantly reduce or eliminate encapsulation, resulting in a prolonged, aesthetically pleasing, soft mound below the breast tissue or pectoralis muscle. In addition, a need exists for implants into which useful substances, such as beneficial medications, chemical agents, hormonal treatments, stem cells, such as adipocytes, cellular precursors and components, and radiation media can be instilled to enhance the treatment capabilities of the implant in cancer and other breast pathology.

BRIEF SUMMARY OF THE INVENTION

The present invention overcomes deficiency of the prior art, such as those noted above, by providing an implant in which at least the outer portion of the implant, and as much as the entire implant, is made of a resorbable material. The implant is sized and shaped to reduce excised tissue. Preferably, the implant provides a support structure in the form of a framework or scaffold for the surrounding tissue after implantation. The support structure preferably is porous to permit the in-growth of fibrous replacement tissue. Advantageously, replacement tissue in-growth takes place without encapsulation and with reduced scarring.

The invention, in one form thereof, is directed to an implant for marking an area within a living body. The implant includes a matrix material and a marking material. The implant is formable to fit the shape and size of a cavity in the human body. The implant is configured to support tissue surrounding the cavity and to allow in-growth of fibrous tissue into and replace at least a portion of the matrix material.

The invention, in another form thereof, is directed to a tissue marking implant. The tissue marking implant includes a matrix and a dye marker. A matrix is collagen material. The matrix has a porous structure for supporting surrounding tissue of a breast and is configured to provide a framework for the in-growth of fibrous tissue into the matrix. The dye marker is supported by the matrix for dispersion into the tissue.

According to an embodiment of the invention, excised tissue is replaced by installing an implant having at least an outer shell of resorbable material. The implant is sized and shaped to replace the excised tissue. The implant supports surrounding tissue while fibrous tissue replaces the resorbable portion of the implant.

In a further development, at least a portion of the implant can be provided in the form of a compressible or non-compressible sponge or foam, or a self-expanding sponge or foam. The sponge or foam provides a porous support matrix for surrounding and in-growing tissue. In the form of a compressible, expandable, or self-expanding sponge or foam, the implant advantageously can be inserted through a cannula or a needle, or optionally can be directly inserted. Additionally, the implant can be instilled with beneficial materials, such as indicated medicaments, therapeutics, or diagnostic agents, as well as matrix enhancing additives.

Other features and advantages of the present invention will become apparent from the following description of the invention which refers to the accompanying drawings.

BRIEF DESCRIPTION OF THE DRAWINGS

FIG. 1 is a schematic elevation of a breast implant according to a preferred embodiment of the present invention.

FIG. 2 is a schematic sectional view of a breast after implantation of the implant of FIG. 1.

FIG. 3 is a schematic sectional view of a breast after implantation of an alternative embodiment of the implant of the present invention.

FIG. 4 is a schematic sectional view of a breast implant according to a second alternative embodiment of the present invention.

FIG. 5 is a schematic sectional view of a breast after implementation of the implant of FIG. 4.

FIG. 6 is a schematic sectional view of a breast implant and a method of insertion according to further alternative embodiments of the present invention, particularly for cases involving the removal of smaller pieces of tissue such as by biopsy and lumpectomy.

DETAILED DESCRIPTION OF THE INVENTION

Referring initially to FIGS. 1 and 2, an implant 2 has an outer shell 4 made of a biosorbable material woven into a mesh. The inner contents of the implant are fluids such as saline and autologous blood products.

Outer shell 4 is made entirely of biosorbable materials, such as collagens or polyglycolic acids, for example. Over a period of approximately three weeks to six months, the outer shell dissolves, leaving the inner contents 6 present inside the breast. Hard encapsulation will not occur because there is not a foreign body contained within the prosthetic space.

Referring to FIG. 3, implantation of an alternative embodiment of implant 2 is illustrated in which the outer shell 4 includes both biosorbable material, and nonabsorbable material, such as monofilament polypropylene fibers. Outer shell 4 is provided as a mesh or weave of the mixed material, surrounding contents 6 as described above. After a resorption period, contents 6 remain surrounded by a skeletal outer shell made up of non-absorbable fibers 8.

Advantageously, the proportions and spacing of the two types of materials can be altered to provide the desired properties of containment using a minimal amount of nonabsorbable material. Accordingly, the non-absorbable fibers 8 which remain after the biosorbable materials resorb will act as a scaffolding to allow the prosthesis to hold its shape; however, because of the limited amount of foreign material, encapsulation and scarring are decreased.

Referring to FIGS. 4 and 5, a second alternative embodiment of the present invention is shown. A prosthesis 10 features two capsules, a larger, outer capsule 12 made of biosorbable materials, and a smaller inner capsule 14 made of anon-absorbable material. Inner capsule 14 also can be made partially resorbable as in the first alternative embodiment above. Outer capsule 12 and inner capsule 14 can be separated by a thin layer 16 of saline or autologous fluids such as those described above. Inner capsule 14 surrounds a more permanent member 18 made of autologous fluids or saline, for example.

After implantation, outer capsule 12 dissolves, thus preventing hardening by encapsulation of the prosthesis. The supply of fluid 16 between the capsules (a few to several c.c.'s) is absorbed by the body once released by the dissolution of outer capsule 12.

Referring to FIG. 6, a further alternative embodiment of the present invention includes an implant prosthesis 20 provided in the form of a matrix framework, such as a sponge or foam. The implant, which preferably is entirely biodegradable (resorbable), has a porous structure which supports the surrounding tissue and provides a framework for the in-growth of fibrous tissue material. FIG. 6 illustrates tissue portion 24 surrounding implant 20 into which marker dye included in the implant, and described further below, has leached over time from the implant, thereby marking the tissue. Accordingly, a surgeon performing a subsequent procedure easily will recognize the tissue surrounding the previous excision.

According to a preferred embodiment, the implant is provided in the form of a foam or sponge which can be modified by a surgeon prior to implantation, such as at a lumpectomy or biopsy site, simply by trimming the sponge to the appropriate size and shape. Alternatively, the implant can be a pre-shaped prosthesis of appropriate size, or an appropriate amount of foam or foam-forming materials. Optionally, the foam can be provided as a self-expanding matrix that either is compressed, or forms in situ. Advantageously, the implant can be modified to correspond to the breast tissue that either has been removed, requires replacement, or requires augmentation. The foam or sponge matrix is sufficiently resilient to support the surrounding tissue without collapsing.

A preferred embodiment of implantation is illustrated schematically in FIG. 6, whereby the implant is elastically compressible, and is delivered using a cannula or needle 22 inserted into the breast. A single implant 20 is shown being compressed so as to fit within cannula 22. A force is applied to drive the compressed implant distally through and out the distal end of the cannula into the implant site, where the resilient implant 20 expands to fill the implant site space.

The force for advancing the sponge or foam material through the cannula can be applied directly to the implant, or indirectly using fluids, for example. Advantageously, the implant can be used in conjunction with stereotactic biopsy instrumentation, such as the ABBI® System, the MIB System by US Surgical, or the Mammotome® System by Johnson and Johnson.

As a further alternative, the sponge or foam implant of the present invention can form all or part of a larger implant, such as those described above. Accordingly, the tissue supporting sponge or foam or foam matrix will form, for example, all or part of the outer shell 4 of implant 2. Implantation using open procedures usually would be indicated when the sponge implant of the present invention is used as all or part of a larger implant. Accordingly, the sponge or implant would be placed directly into the biopsy or lumpectomy cavity.

In addition, the implant 20 can be provided in the form of a self-expanding foam, which can be injected through a tubular member 22 such as a needle or cannula in a metered amount. An appropriate amount of foam-forming materials can be inserted through cannula 22 and allowed to expand or form a matrix within the cavity created by the excised tissue. Alternatively, a specialized, applicator may be used to inject the desired amount of the foam. The amount of foam is preselected to allow sufficient expansion to fill the void left by the excision and support the surrounding tissue to prevent dimpling.

Following insertion of the implant, such as by an open method or one of the stereotactic methods described above, the resorbable implant occupies the breast tissue cavity and supports the surrounding tissue until such time as it resorbs or biodegrades. After initial implantation, the patient's own fluids, fibroblast, and stem cells, such adipocytes, vascular stem cells, and others, permeates the sponge prosthesis. In the case of a small implant, such permeation would occur naturally, subsequent to implantation. In the case of a larger implant, providing the implant at least partially filled with fluids prior to implantation may be indicated.

Advantageously, the new prosthesis decreases encapsulation after implantation. Various biosorbable materials can be used in the implant of the present invention. Known biosorbable materials include polyglycolic acid (Dexon, Davis & Geck); polyglactin material (Vicryl, Ethicon); poliglecaprone (Monocryl, Ethicon); and synthetic absorbable lactomer 9-1 (Polysorb, United States Surgical Corporation)

Other foamable materials that can be utilized in the present invention include, without limitation, proteins such as collagen, fibronectin, laminin and fibrin, most preferably collagen, and high molecular weight polysaccharides, such as heparan sulphate, chondroitin sulphate, hyaluronic acid and dermatan sulphate. Mixtures of any of the aforementioned materials also can be used, as required.

The materials can be modified, by cross-linking for example, to control degradation rates over varying lengths of time, after which they are substantially or completely resorbed.

Foams can be formed by various means known to those skilled in the art, including injecting an aerosol into a gel, and freeze-drying aqueous dispersions of the foam-forming material. Foaming agents can be included to promote formation of the foam. In addition, stabilizing agents can be included to enhance foam stability. The foams can be extruded or formed in situ.

According to the present invention, these products may be mixed with one another or combined to provide various resorption times or gradients, and/or may be interrelated with non-absorbable materials, such as polypropylene or PTFE (polytetrafluoroethylene) sold as (Gore-Tex®) material, for example. In an instance where a non-absorbable material is utilized, the non-resorbable implant section will remain partially intact as a permanent structure.

In each of the embodiment, the resorbable portions of the prosthesis ultimately biodegrades, and the patient is left with autologous tissue, some of which may have been implanted, or a permanent implant such as saline, as a filler for the biopsy cavity, thus preserving the contour of the breast and preventing indentation of the overlying skin.

The implants of the present invention further can be instilled, before or after implantation, with indicated medicines and other chemical or diagnostic agents. Examples of such agents include, but are not limited to, antibiotics, chemotherapies, other cancer therapies, brachytherapeutic material for local radiation effect, x-ray opaque or metallic material for identification of the area, hemostatic material for control of bleeding, growth factor hormones, immune system factors, gene therapies, biochemical indicators or vectors, and other types of therapeutic or diagnostic materials which may enhance the treatment of the patient.

The breast implant preferably includes a permanent or temporary dye marker such as, but not limited to, indigo carmine or methylene blue. This marker serves as a visual identification of the area that has been biopsied or a lumpectomy has been performed so that in the future an operating surgeon can identify the surrounding tissue before he violates the previously biopsied cavity. These dyes leach into the breast tissue giving the surgeon an indication when he is nearing the point of interest, that being a previous biopsy site particularly if it is positive for a cancer or if it is a site for which a lumpectomy has been previously performed and the pathologist advises us that there is residual cancer. The surgeon can thus remove any of the surrounding breast tissue that contains dye and depending upon its concentration and the distance that it has traveled from the biopsy site will give us an indication of how much tissue should appropriately be removed.

This dye may be integrated with a bioabsorbable material such as, but not limited to collagen or may be in a separate capsule that is inserted with the bioabsorbable material as well as a metallic device for radiographic identification.

These two dyes are very dark colored dyes and these do leach through the breast tissue but will not stain the overlying skin.

The present invention has been described particularly in connection with a breast implant, but it will be obvious to those of skill in the art that the invention can have application to other parts of the body, such as the face, and generally to other soft tissue or bone. Accordingly, the invention is applicable to replacing missing or damaged soft tissue, structural tissue or bone, or for cosmetic tissue or bone replacement.

Although the present invention has been described in relation to particular embodiments thereof, many other variations and modifications and other uses will become apparent to those skilled in the art. It is preferred, therefore, that the present invention be limited not only by the specific disclosure herein, but only by the appended claims.

What is claimed is:

1. An implant for marking an area within a living body comprising a matrix material and a marking material, the implant being formable to fit the shape and size of a cavity in the human body, the implant being configured to support tissue surrounding the cavity and to allow in-growth of fibrous tissue into and replace at least a portion of the matrix material, wherein the marking material is a dye and the dye is one of indigo carmine and methylene blue.

2. An implant for marking an area within a living body comprising a matrix material and a marking material, the implant being formable to fit the shape and size of a cavity in the human body, the implant being configured to support tissue surrounding the cavity and to allow in-growth of fibrous tissue into and replace at least a portion of the matrix material, wherein the matrix material comprises one of a self-expanding foam, a compressible foam or sponge, and a non-compressible foam or sponge.

3. An implant for marking an area within a living body comprising a matrix material and a marking material, the implant being formable to fit the shape and size of a cavity in the human body, the implant being configured to support tissue surrounding the cavity and to allow in-growth of fibrous tissue into and replace at least a portion of the matrix material, wherein the matrix material comprises a foamed bioabsorbable protein.

4. An implant for marking an area within a living body comprising a matrix material and a marking material, the implant being formable to fit the shape and size of a cavity in the human body, the implant being configured to support tissue surrounding the cavity and to allow in-growth of fibrous tissue into and replace at least a portion of the matrix material, wherein the matrix material comprises of a foamed collagen.

5. An implant for marking an area within a living body comprising a matrix material and a marking material, the implant being formable to fit the shape and size of a cavity in the human body, the implant being configured to support tissue surrounding the cavity and to allow in-growth of fibrous tissue into and replace at least a portion of the matrix material, and a shell containing the matrix material.

6. The implant of claim 5, wherein the shell comprises compressed matrix material.

7. The implant of claim 5, wherein the shell completely surrounds the matrix material.

* * * * *